United States Patent
Ishino et al.

(10) Patent No.: US 6,355,236 B2
(45) Date of Patent: *Mar. 12, 2002

(54) SUSTAINED RELEASE PHEROMONE FORMATION

(75) Inventors: Tatsuya Ishino; Ryuichi Saguchi, both of Niigata-ken (JP)

(73) Assignee: Shin-Etsu Chemical Co., Ltd. (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/240,580

(22) Filed: Feb. 1, 1999

(30) Foreign Application Priority Data

Jan. 30, 1998 (JP) .......................... 10-019769

(51) Int. Cl.$^7$ ............................... A01N 25/00
(52) U.S. Cl. ................... 424/84; 424/405; 424/409; 424/412
(58) Field of Search ................. 424/405, 84, 409, 424/412

(56) References Cited

U.S. PATENT DOCUMENTS 4,734,281 A * 3/1988 Yakamoto et al. .......... 424/408
4,923,119 A * 5/1990 Yamamoto et al. .......... 239/55

FOREIGN PATENT DOCUMENTS

EP          0 236 188          9/1987

OTHER PUBLICATIONS

Database WPI, Section Ch, Week 8243, Derwent Publications Ltd., London, GB; AN 82–91395E XP002107753 & JP 57 150603 A (Nitto Electric Ind Co) Sep. 17, 1982.

* cited by examiner

Primary Examiner—Thurman K. Page
Assistant Examiner—Lakshmi S. Channavajjala
(74) Attorney, Agent, or Firm—Burns, Doane, Swecker & Mathis, L.L.P.

(57) ABSTRACT

The present invention provides a sustained release pheromone formation comprising the sex pheromone substance which is an aldehyde compound wherein the formation can prevent the degradataion of the aldehyde compound and release the compound at an uniformed rate during the control term of the subjective pest insects. The sustained release pheromone formation is obtained by mixing an aliphatic derivative of which number of carbon atoms is equal to or less than that of the sex pheromone substance with a $C_{10-18}$ aldehyde which is a sex pheromone and then filling the resulting liquid mixture in a plastic container.

7 Claims, 1 Drawing Sheet

SUSTAINED RELEASE PHEROMONE FORMATION

BACKGROUND OF THE INVENTION

1. Field of the Invention

The present invention is related to a sustained release pheromone formation to be used in a so-called mating disruption method, that is, a method for controlling pest insects by releasing the sex pheromone of the pest insects over the field, thereby disrupting their mating.

2. Description of the Related Art

Controlling pest insects by disruption of mating is carried out by releasing the artificially synthesized sex pheromone of the target pest insects in the air and disturbing the communication between males and females to decrease a mating ratio, thereby controlling the appearance of the next generation. The sustained release formation of a sex pheromone is required to have a performance permitting the stable release of the sex pheromone during the generation stage of pest insects. The release of sustained release pheromone formation is controlled at a predetermined rate for a long time by putting the formation with one or more components of the sex pheromone or geometric isomer thereof in a plastic container and then permeating the mixture through the plastic film of the container.

The sex pheromone of pest insects such as *Chilo suppressalis, Helicoverpa assulata* and *Helicoverpa armigera* is an aliphatic aldehyde compound having 10 to 18 carbon atoms. Using the above-described sustained release formation, the release rate decreases because the aldehyde compounds easily undergo degradation such as oxidation, polymerization or the like. As a countermeasure against it, a stabilizer such as antioxidant or polymerization inhibitor is added. The antioxidant or polymerization inhibitor is effective for stabilizing the liquid of the formation in a plastic container, but exhibits no effects for the aldehyde compound once permeated from the container. The aldehyde compound permeated from the container undergoes polymerization reaction on the outer surface of the container and forms a polymer layer, which markedly decreases the release rate of the aldehyde compound from the container. It is therefore necessary to install the sustained release formations plural times during the control term of pest insects, which inevitably increases the application labor.

SUMMARY OF THE INVENTION

As a solution to these problems, the present invention has been completed. An object of the present invention is to provide a sustained release pheromone formation comprising an aldehyde compound, which formation is capable of preventing the degradation of the aldehyde compound, thereby releasing the aldehyde compound at an uniformed rate during the control term of pest insects.

The sustained release pheromone formation of the present invention which has been completed with a view to attaining the above-described object is obtained by filling, in a plastic container, a liquid mixture of a sex pheromone which is in the liquid form and is a $C_{10-18}$ aldehyde and an aliphatic derivative of which number of carbon atoms is equal to or less than that of the aldehyde.

To sustained release pheromone formation according to the present invention is applicable to the disruption of mating of any insects that have at least a sex pheromone which is a $C_{10-18}$ aldehyde. Examples of the insects to which the sustained release pheromone formation of the present invention is applicable include Chilo, Choristoneura, Helicoverpa, Heliothis, Parapediasia, Plutella and Platyptilia genera. The formation is particularly useful for the control of *Chilo suppressalis, Choristoneura fumiferana, Helicoverpa assulta, Helicoverpa armigera, Heliothis virescens, Heliothis zea, Parapediasia teterrella, Plutella xylostella* and *Platyptilia carduidactyla*.

The present invention can be carried out suitably by using, as the aliphatic derivative, an aliphatic acetate of which number of carbon atoms is less than that of the aldehyde by 2 to 4, an aliphatic alcohol of which number of carbon atoms is less than that of the aldehyde by 2 to 6 or an aliphatic carboxylate ester of which number of carbon atoms is equal to or less than that of the aldehyde by 1 to 4. Since each of the above-described aliphatic derivatives has physical properties, such as film permeability and vapor pressure, similar to the aldehyde, it is released and evaporated from the formation together with the aldehyde, which prevents the retention of the aldehyde on the surface of the formation. In addition, the aliphatic derivative prevents the degradataion of the aldehyde, because it is mixed at a proper concentration in the formation.

As the aliphatic derivative, usable is one or more than one aliphatic derivatives selected from the following (i) to (iii):

(i) an aliphatic acetate of which number of carbon atoms is less than that of the sex pheromone substance by 2 to 4, (ii) an aliphatic alcohol of which number of carbon atoms is less than that of the sex pheromone substance by 2 to 6, and (iii) an aliphatic carboxylate ester of which number of carbon atoms is equal or less than that of the sex pheromone substance by 1 to 4.

Examples of the aliphatic acetate of which number of carbon atoms is less than that of the sex pheromone substance by 2 to 4 include aliphatic acetates having a linear, branched or cyclic alkyl or alkylene group having 6 to 16 carbon atoms, particularly 10 to 16 carbon atoms. Among them, the aliphatic acetates having a linear alkyl or alkylene group are preferred.

Examples of the linear, branched or cyclic alkyl group having 6 to 16 carbon atoms include hexyl, heptyl, octyl, nonyl, decyl, undecyl, dodecyl, tridecyl, tetradecyl, pentadecyl, hexadecyl, methylpentyl, methylhexyl, methylheptyl, methyloctyl, methylnonyl, methyldecyl, methylundecyl, methyldodecyl, methyltridecyl, methyltetradecyl, methylpentadecyl, ethylbutyl, ethylpentyl, ethylheptyl, ethyloctyl, ethylnonyl, ethyldecyl, ethylundecyl, ethyldodecyl, ethyltridecyl, ethyltetradecyl, dimethylbutyl, dimethylpentyl, dimethylheptyl, deimthyloctyl, dimethylnonyl, dimethyldecyl, dimethylundecyl, dimethyldodecyl, dimethyltridecyl, dimethyltetradecyl, propylpentyl, propylhexyl, propylheptyl, propyloctyl, propylnonyl, propyldecyl, propylundecyl, propyltridecyl, ethylmethylpentyl, ethylmethylhexyl, ethylmethylheptyl, ethylmethyloctyl, ethylmethylnonyl, ethylmethyldecyl, ethylmethylundecyl, ethylmethyldodecyl, ethylmethyltridecyl, diethylpentyl, diethylhexyl, diethylheptyl, diethylnonyl, diethyldecyl, diethylundecyl, diethyldodecyl and cyclohexadecyl groups.

Examples of the linear, branched or cyclic alkylene group having 6 to 16 carbon atoms include hexenyl, heptenyl, octenyl, nonenyl, decenyl, undecenyl, dodecenyl, tridecenyl, tetradecenyl, pentadecenyl, hexadecenyl, methylpentenyl, methylhexenyl, methylheptenyl, methyloctenyl, methylnonenyl, methyldecenyl, methylundecenyl, methyldodecenyl, methyltridecenyl, methyletetradenecyl, methylpentadecenyl, ethylbutenyl, ethylpentenyl, ethylheptenyl, ethyloctenyl, ethylnonenyl, ethyldecenyl, ethylundecenyl, ethyldodecenyl, ethyltridecenyl, ethyltetradecenyl, dimethylbutenyl, dimethylpentenyl, dimethylheptenyl, dimethyloctenyl, dimethylnonenyl, dimethyldecenyl, dimethylundecenyl, dimethyldodecenyl, dimethyltridecenyl, dimethyltetradecenyl, propylpentenyl, propylhexenyl, propylheptenyl, propyloctenyl, propylnonenyl, propyldecenyl, popylundecenyl, propyltridecenyl, ethylmethylpentenyl, ethylmethylhexenyl, ethylmethylheptenyl, ethylmethyloctenyl, ethylmethylnonenyl, ethylmethyldecenyl, ethylmethylundecenyl, ethyl methyldodecenyl, ethyl methyltridecenyl, diethylnonenyl, diethyldecenyl, diethylundecenyl, diethyldodecenyl, hexadienyl, heptadienyl, octadienyl, nonadienyl, decadienyl, undecadienyl, dodecadienyl, tridecadienyl, tetradecadienyl, pentadecadienyl, hexadecadienyl, methylpentadienyl, methylhexadienyl, methylheptadienyl, methyloctadienyl, methylnonadienyl, methyldecadienyl, methylundecadienyl, methyldodecadienyl, methyltridecadienyl, methyltetradecadienyl, methylpentadecadienyl, ethylbutadienyl, ethylpentadienyl, ethylheptadienyl, ethylocatadienyl, ethylnonadienyl, ethyldecadienyl, ethylundecadienyl, ethyldodecadienyl, ethyltridecadienyl, ethyletradecadienyl, dimethylbutadienyl, dimethylpentadienyl, dimethylheptadienyl, dimethylocatadienyl, dimethylnonadienyl, dimethyldecadienyl, dimethylundecadienyl, dimethyldodecadienyl, dimethyltridecadienyl, dimethyltetradecadienyl, propylpentadienyl, propylhexadienyl, propylheptadienyl, propyloctadienyl, propylnonadienyl, propyldecadienyl, propylundecadienyl, propyltridecadienyl, ethylmethylpentadienyl, ethylmethylhexadienyl, ethylmethylheptadienyl, ethylmethyloctadienyl, ethylmethylnonadienyl, ethylmethyldecadienyl, ethylmethylundecadienyl, ethylmethyldodecadienyl, ethylmethyltridecadienyl, diethylpentadienyl, diethylhexadienyl, diethylheptadienyl, diethylnonadienyl, diethyldecadienyl, diethylundecadienyl, dimethyldodecadienyl and cyclohexadienyl groups.

Specific examples of the aliphatic acetate of which number of carbon atoms is less than that of the sex pheromone substance by 2 to 6 include decyl acetate, undecyl acetate, dodecyl acetate, tridecyl acetate, tetradecyl acetate, pentadecyl acetate, hexadecyl acetate, decenyl acetate, undecenyl acetate, dodecenyl acetate, tridecenyl acetate, tetradecenyl acetate, pentadecenyl acetate and hexadecenyl acetate.

Examples of the aliphatic alcohol of which number of carbon atoms is less than that of the sex pheromone substance by 2 to 6 include aliphatic alcohols having a linear, branched or cyclic alkyl or alkylene group having 4 to 16 carbon atoms, particularly 8 to 16 carbon atoms. Among them, the aliphatic alcohols having a linear alkyl or alkylene group are preferred.

Examples of the linear, branched or cyclic alkyl group having 4 to 16 carbon atoms include, in addition to the above-exemplified linear, branched or cyclic alkyl groups having 6 to 16 carbon atoms, butyl, pentyl, methylpropyl, methylbutyl, cyclobutyl and cyclopentyl groups.

Examples of the linear, branched or cyclic alkylene group having 4 to 16 carbon atoms include, in addition to the above-exemplified linear, branched or cyclic alkylene groups having 6 to 16 carbon atoms, butenyl, pentenyl, methylpropenyl, methylbutenyl, cyclobutenyl, cyclopentenyl, butadienyl, pentadienyl, methylpropadienyl, methylbutadienyl, cyclobutadienyl and cyclopentadienyl groups.

Specific examples of the aliphatic alcohol of which number of carbon atoms is less than that of the sex pheromone substance by 2 to 6 include octanol, nonanol, decanol, undecanol, dodecanol, tridecanol, tetradecanol, pentadecanol, hexadecanol, octenol, nonenol, decenol, undecenol, dodecenol, tridecenol, tetradecenol, pentadecenol and hexadecenol.

Examples of the aliphatic carboxylate ester of which number of carbon atoms is equal to or less than that of the sex pheromone substance by 1 to 4 include aliphatic carboxylate esters having a linear, branched or cyclic alkyl or alkylene group having 6 to 18 carbon atoms, particularly 10 to 18 carbon atoms. Among them, the aliphatic carboxylate esters having a linear alkyl or alkylene group are preferred.

Examples of the linear, branched or cyclic alkyl group having 6 to 18 carbon atoms include, in addition to the above-exemplified linear, branched or cyclic alkyl groups having 4 to 16 carbon atoms, heptadecyl, octadecyl, methylhexadecyl, methylheptadecyl, ethylpentadecyl, ethylhexadecyl, dimethylpentadecyl, dimethylhexadecyl, propyltetradecyl, propylpentadecyl, ethylmethyltetradecyl, ethylmethylpentadecyl, diethyltridecyl and diethyltetradecyl groups.

Examples of the linear, branched or cyclic alkylene group having 6 to 18 carbon atoms include, in addition to the above-exemplified linear, branched or cyclic alkylene groups having 4 to 16 carbon atoms, heptadecenyl, octadecenyl, methylhexadecenyl, methylheptadecenyl, ethylpentadecenyl, ethylhexadecenyl, dimethylpentadecenyl, dimethylhexadecenyl, propyltetradecenyl, propylpentadecenyl, ethylmethyltetradecenyl, ethylmethylpentadecenyl, diethyltridecenyl, diethyltetradecenyl, heptadecadienyl, octadecadienyl, methylhexadecadienyl, methylheptadecadienyl, ethylpentadecadienyl, ethylhexadecadienyl, propyltetradecadienyl, propylpentadecadienyl, ethylmethyltetradecadienyl, ethylmethylpentadecadienyl, diethyltridecadienyl and diethyltetradecadienyl groups.

Specific examples of the aliphatic carboxylate ester of which number of carbon atoms is equal to or less than that of the sex pheromone substance by 1 to 4 include methyl laurate, ethyl laurate, methyl myristate, ethyl myristate, methyl palmitate and ethyl palmitate.

Incidentally, the aliphatic derivative can be used as a combination with more than one substance selected from the above-described (i) to (iii).

Incidentally, the aliphatic derivative can be used as a combination with more than one substance selected from the above-described (i) to (iii).

When the aliphatic derivative has carbon atoms more than the above-described range, the release of the aliphatic derivative becomes inferior to that of the aldehyde, inevitably leading to the retention of the aldehyde on the outer surface of the formation and formation of a polymer layer. Moreover, the composition ratio of the aliphatic derivative in the formation increases, which dilutes the aldehyde, thereby deteriorating its release. As a result, the formation does not exhibit uniform release. The number of carbon atoms exceeding the above range is therefore not preferred.

When the aliphatic derivative has carbon atoms less than the above-described range, on the other hand, the release of the aliphatic derivative exceeds that of the aldehyde, which controls the release of the aldehyde and causes enrichment of the aldehyde, leading to the polymerization reaction. As a result, the formation does not exhibit uniform release. The number of carbon atoms less than the above range is therefore not preferred.

The present invention can be suitably carried out when the weight ratio of the sex pheromone substance to the aliphatic derivative ranges from 95:5 to 50:50, preferably 90:10 to 60:40. When the weight ratio of the sex pheromone substance is less than 50:50, the released amount of the sex pheromone substance per one formation decreases. In this case, it is necessary to increase the number of formations to be applied per unit area. When the ratio exceeds 95:5, on the other hand, the release amount of the sex pheromone substance is out of control and it retains on the outer surface of the formation and forms a polymer layer, which inevitably prevents the continuous release of the sex pheromone substance in a fixed amount.

As the sex pheromone substance, usable in the present invention is at least one aliphatic aldehyde selected from the group consisting of Z5-decenal, n-dodecanal, Z5-dodecanal, Z7-dodecenal, Z9-dodecenal, E5Z7-dodecadienal, Z5E7-dodecadienal, Z5Z7-dodecadienal, E7Z9-dodecadienal, E8E10-dodecadienal, E8Z10-dodecadienal, Z8E10-dodecadienal, E9,11-dodecadienal, Z9,11-dodecadienal, n-tetradecanal, Z5-tetradecenal, Z7-tetradecenal, Z9-tetradecenal, E11-tetradecenal, Z11-tetradecenal, E8E10-tetradecadienal, Z9E12-tetradecadienal, Z9Z11-tetradecadienal, Z9E12-tetradecadienal, E11,13-tetradecadienal, Z11,13-tetradecadienal, Z9E11,13-tetradecatrienal, Z10-pentadecenal, E9Z11-pentadecadienal, n-hexadecanal, Z7-hexadecenal, Z9-hexadecenal, E10-hexadecenal, Z10-hexadecenal, E11-hexadecenal, Z11-hexadecenal, E6Z11-hexadecadienal, Z7E11-hexadecadienal, Z7Z11-hexadecadienal, E9Z11-hexadecadienal, Z9E11-hexadecadienal, Z9E12-hexadecadienal, E10E12-hexadecadienal, E10Z12-hexadecadienal, Z10E12-hexadecadienal, E11E13-hexadecadienal, E11Z13-hexadecadienal, Z11E13-hexadecadienal, Z11Z13-hexadecadienal, E4E6Z11-hexadecatrienal, E10E12E14-hexadecatrienal, E10E12Z14-hexadecatrienal, n-octadecanal, E2-octadecanal, Z9-octadecenal, E11-octadecenal, Z11-octadecenal, E13-octadecenal, Z13-octadecenal, E14-octadecenal, E2Z13-octadecadienal, Z3Z13-octadecadienal, Z9Z12-octadecadienal, E11E14-octadecadienal, Z13Z15-octadecadienal and Z9Z12Z15-octadecatrienal.

Among them, n-tetradecanal, Z7-tetradecenal, E7-tetradecenal, Z9-tetradecenal, E9-tetradecenal, Z11-tetradecenal, E11-tetradecenal, n-hexadecanal, Z7-hexadecenal, E7-hexadecenal, Z9-hexadecenal, E9-hexadecenal, Z11-hexadecenal, E11-hexadecenal, n-octadecanal, Z9-octadecenal, E9-octadecenal, Z11-octadecenal, E11-octadecenal, Z13-octadecenal and Z13-octadecenal are particularly preferred.

The plastic container used in the present invention is made of a polyolefin polymer. Examples of the polyolefin polymer such as polyethylene, polypropylene and copolymers containing at least 90% of ethylene such as ethylene-vinyl acetate copolymer and ethylene-acrylate ester copolymer. The above-exemplified material permits the permeation of the sex pheromone substance of aliphatic compound and the release of it from the film at a proper rate.

The plastic container is in the form of a tube, capsule, ampoule or bag. Among them, the container in the tubular form is most preferred, because it permits the uniform release of the sex pheromone substance for a long time. The release at a proper rate can be maintained when the tube has an internal diameter of 0.5 to 2.0 mm, preferably 0.6 to 1.6 mm and has a wall thickness of 0.2 to 1.0 mm, preferably 0.3 to 0.8 mm.

The sustained release pheromone formation according to the present invention is thus effective for preventing the degradataion of the sex pheromone substance, whereby uniform release can be attained. The release rate can be controlled by adjusting the mixing ratio of the sex pheromone substance with the aliphatic derivative.

Production examples of the sustained release pheromone formation according to the present invention will be described below. It should however be borne in mind that the present invention is not limited to these production examples. It is possible for those skilled in the art to modify the shape or production process of the plastic container, arrangement of the sustained release formations or the like as needed depending on the field or kind of the pest insect to which the invention substance is applied.

The plastic container, more specifically, a polyethylene tube having a uniformed internal diameter and wall thickness is produced by extrusion. The sustained release formation is produced by preparing a liquid mixture wherein an aliphatic aldehyde and an aliphatic acetate have been mixed in a predetermined ratio, injecting the liquid mixture into the polyethylene tube from one end thereof, heat sealing both ends of the tube by a thermal trowel under pressure and then cutting each of the sealed portions of the tube. In the field to be subjected to pest insect control, the sustained pheromone formations are arranged at equal intervals so as to accomplish the uniform release of a necessary amount of the sex pheromone substance over the field.

BRIEF DESCRIPTON OF THE DRAWINGS

DETAILED DESCRIPTION OF THE PREFERRED EMBODIMENT

Figure 1:
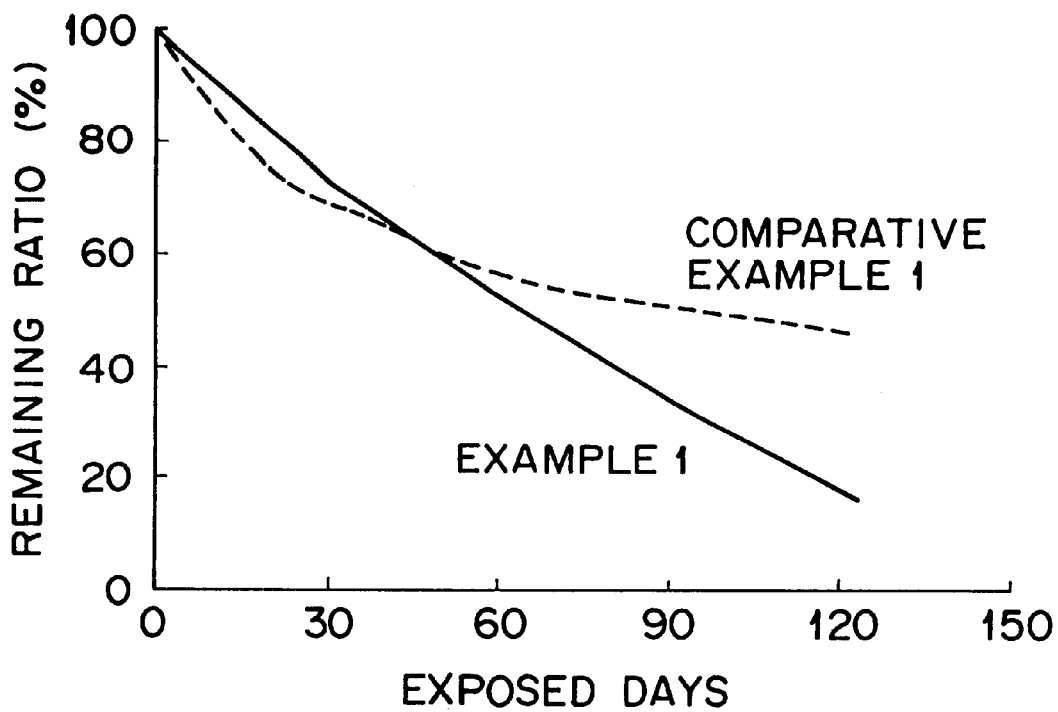
FIG. 1 illustrates a time-dependent change of the remaining ratio of the sex pheromone substance of *Chilo suppressalis* in the sustained release pheromone formation.

The present invention will hereinafter be described more specifically by examples. It should however be borne in mind that the present invention is not limited to or by them. Incidentally, prepared in Example 1 is a sustained release formation composed of three aldehyde components and an aliphatic acetate, while prepared in Comparative Example 1 is that composed solely of the three aldehyde components employed in Example 1. A time-dependent change of the formation after application in the paddy field is shown in each example.

EXAMPLE 1

A liquid mixture was prepared by mixing 7 parts by weight of a sex pheromone substance of *Chilo suppressalis* composed of 77 wt. % of Z11-hexadecenal (Z11–16: Ald), 8 wt. % of Z9-hexadecenal (Z9–16: Ald) and 15 wt. % of Z13-octadecenal (Z13–18: Ald) and 3 parts by weight of n-tetradecyl acetate (n-14: Ac). One end of a plastic container (polyethylene tube) having an internal diameter of 1.40 mm and outer diameter of 2.60 mm was immersed in the resulting liquid mixture and the liquid mixture was injected therefrom into the container by suction. The container was heat sealed by a thermal trowel at every 200 mm under pressure and each of the sealed portions was cut for separation, whereby sex pheromone formations were produced by way of trial. The amount of the liquid mixture filled in each of the formations was 240 mg, of which 168 mg was the sex pheromone substance of *Chilo suppressalis*.

Each of the resulting formations was attached to a rod and then, in the paddy field, exposed at 30 to 50 cm high from the ground from May to September. Every month, five formations were collected and the remaining amounts of Z11-hexadecenal, Z9-hexadecenal and Z13-octradecenal in the plastic container were measured. The measurement was carried out by cutting the collected formations into 1.5 cm pieces, immersing them in acetone for 24 hours and analyzing the acetone solution by gas chromatography in accordance with the internal standard method. The total amount of those three aldehyde components was designated as the amount of the sex pheromone substance of *Chilo suppressalis* and the remaining ratio was calculated by comparing the remaining amount with the filled amount. The results are shown in FIG. 1.

Comparative Example 1

Sustained release pheromone formations each containing 240 mg of only a sex pheromone substance of *Chilo suppressalis* was produced by way of trial by filling 77 wt. % of Z11-hexadecenal (Z11–16: Ald), 8 wt. % of Z9-hexadecenal (Z9–16: Ald) and 15 wt. % of Z13-octadecenal (Z13–18: Ald) in a plastic container similar to that used in Example 1. These formations were applicated in the same field on the same day with those of Example 1 and were collected on the same day. The remaining ratio was calculated in a similar manner to Example 1. The results are shown in FIG. 1.

As can be seen from FIG. 1, it has been found that the formations of Example 1 released the sex pheromone substance at an uniformed rate, while the release rate of the sex pheromone substance from those of Comparative Example 1 lowered with the passage of time.

The sustained pheromone formations in Examples 2, 3 and 4 contain the same aldehyde and, as the aliphatic derivative, an aliphatic acetate, an aliphatic alcohol and an aliphatic carboxylate ester, respectively, while the sustained pheromone formation in Comparative Example 1 is composed solely of the same aldehyde as above. A change with the passage of time under predetermined conditions was indicated.

EXAMPLE 2

Sustained release pheromone formations were produced by way of trial by filling 50 wt. % of Z11-hexadecenal as a sex pheromone substance of *Chilo suppressalis*, and 50 wt. % of n-tetradecyl acetate in a plastic container similar to that used in Example 1. The amount of the liquid mixture filled in the container was 240 mg per formation, of which 120 mg was Z11-hexadecenal.

The resulting formations were left to stand under environmental conditions of the temperature of 30° C. and the wind velocity of 1.0 m/sec. Until Day 30, formations were collected every 5 days and then, until Day 150, two formations were collected every 10 days and the amount of Z11-hexadecenal remaining in each formation was measured. The measurement was carried out by cutting the collected formation into 1.5 cm pieces, immersing the resulting pieces in acetone for 24 hours and then analyzing the acetone solution by gas chromatography in accordance with the internal standard method. The remaining ratio was calculated from the comparison of the remaining amount with the filled amount of Z11-hexadecenal. The results are shown in FIG. 2.

Comparative Example 2

Sustained release pheromone formations were produced by way of trial by filling 240 mg per formation of Z11-hexadecenal in a plastic container similar to that used in Example 1. The remaining amount of Z11-hexadecenal was measured with the passage of time under similar conditions to Example 2 and based on it, the remaining ratio was calculated. The results are shown in FIG. 2.

Figure 2:
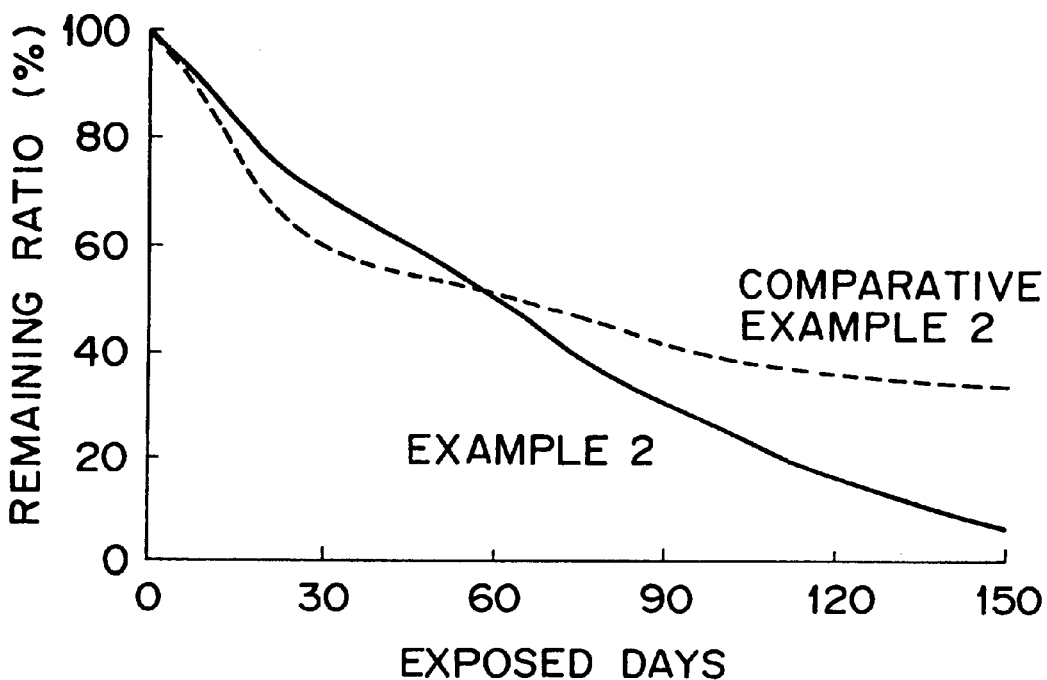
FIG. 2 illustrates another time-dependent change of the remaining ratio of the sex pheromone substance of *Chilo suppressalis* in the sustained release pheromone formation.

As can be seen from FIG. 2, it has been found that the formations obtained in Example 2 exhibited an uniformed release rate irrespective of the passage of time, while the release rate of the formations obtained in Comparative Example 2 decreased with the passage of time.

EXAMPLE 3

Sustained release pheromone formations were produced by way of trial by filling 50 wt. % of Z11-hexadecenal and 50 wt. % of n-dodecanol (n-12: OH) in a plastic container similar to that used in Example 1. The amount of the liquid mixture filled in the container was 240 mg per formation, of which 120 mg was Z11-hexadecenal. The remaining amount of Z11-hexadecenal was measured under similar conditions to Example 2 with the passage of time and based on it, the remaining ratio was calculated. As a result, the formations released Z11-hexadecenal at a predetermined rate irrespective of the passage of time.

EXAMPLE 4

Sustained release pheromone formations were produced by way of trial by filling 50 wt. % of Z11-hexadecenal and 50 wt. % of ethyl laurate ($CH_3(CH_2)_{10}COOC_2H_5$) in a plastic container similar to that used in Example 1. The amount of the liquid mixture filled in the container was 240 mg per formation, of which 120 mg was Z11-hexadecenal. The remaining amount of Z11-hexadecenal was measured under similar conditions to Example 2 with the passage of time and based on it, the remaining ratio was calculated. As a result, the formations released Z11-hexadecenal at a predetermined rate irrespective of the passage of time.

As described above, the sustained release pheromone formation according to the present invention is effective for preventing the degradataion of an aliphatic aldehyde which is a sex pheromone substance and after application, is able to release the substance at an uniformed rate even after the passage of time. It is possible to control the release rate by adjusting the mixing ratio of the sex pheromone substance with an aliphatic derivative. Accordingly, the substance can be released at an uniformed rate for the term (about 5 months) necessary for the control of pest insects. In addition, the conventional sustained release formation has so far been placed several times within the control term of pest insects, but by the use of the sustained release formation of the present invention, such a labor can be reduced and moreover, the use of the sex pheromone substances in excess can be avoided.

What is claimed is:

1. A sustained release pheromone composition obtained by placing in a plastic container a liquid mixture of:
    (i) a sex pheromone substance that is a $C_{10-18}$ aldehyde; and
    (ii) an aliphatic derivative selected from the group consisting of an aliphatic acetate which has 2 to 4 fewer carbon atoms than that of the sex pheromone substance, an aliphatic alcohol which has 2 to 6 fewer carbon atoms than that of the sex pheromone substance and an aliphatic carboxylate ester which has 1 to 4 fewer carbon atoms than that of the sex pheromone substance.

2. A sustained release pheromone composition according to claim 1, wherein said aliphatic derivative is one or more than one substance selected from the following (i) to (iii):
    (i) an aliphatic acetate of which number of carbon atoms is less than that of the sex pheromone substance by 2 to 4, (ii) an aliphatic alcohol of which number of carbon atoms is less than that of the sex pheromone substance by 2 to 6, and (iii) an aliphatic carboxylate ester of which number carbon atoms is equal to or less than that of the sex pheromone substance by 1 to 4.

3. A sustained release pheromone composition according to claim 1, wherein said plastic container comprises a polyolefin polymer and is in the form of a tube, capsule, ampoule or bag.

4. A sustained release pheromone composition according to claim 2, wherein said plastic container comprises a polyolefin polymer and is in the form of a tube, capsule, ampoule or bag.

5. A sustained release pheromone composition obtained by placing in a plastic container a liquid mixture of:

(i) a sex pheromone substance that is a $C_{10-18}$ aldehyde; and (ii) an aliphatic derivative selected from the group consisting of an aliphatic acetate which has 2 to 4 fewer carbon atoms than that of the sex pheromone substance, an aliphatic alcohol which has 2 to 6 fewer carbon atoms than that of the sex pheromone substance and an aliphatic carboxylate ester which has 1 to 4 fewer carbon atoms than that of the sex pheromone substance.

wherein the film permeability and vapor pressure of said aliphatic derivative is similar to that of said sex pheromone substance.

6. The sustained release pheromone composition according to claim 5, wherein said plastic container comprises a polyolefin polymer and is in the form of a tube, capsule, ampoule or bag.

7. The sustained release pheromone composition according to claim 5, wherein said plastic container comprises a polyolefin polymer and is in the form of a tube, capsule, ampoule or bag.

* * * * *